United States Patent

Marschall et al.

[11] Patent Number: 5,380,824
[45] Date of Patent: Jan. 10, 1995

[54] ONE-STEP, ONE-CONTAINER METHOD FOR THE PREPARATION OF PYRIDOXYLATED HEMOGLOBIN

[75] Inventors: Robert Marschall, Sundbyberg; Rainer Eketorp, Danderyd, both of Sweden

[73] Assignee: Pharmacia Aktiebolag, Uppsala, Sweden

[21] Appl. No.: 927,419

[22] PCT Filed: Mar. 21, 1991

[86] PCT No.: PCT/SE91/00221
§ 371 Date: Dec. 15, 1993
§ 102(e) Date: Dec. 15, 1993

[87] PCT Pub. No.: WO91/16352
PCT Pub. Date: Oct. 31, 1991

[30] Foreign Application Priority Data

Apr. 18, 1990 [SE] Sweden .................. 9001378-0

[51] Int. Cl.⁶ .............................................. A61K 35/14
[52] U.S. Cl. ....................................................... 530/385
[58] Field of Search ........................ 530/385; 514/2, 6

[56] References Cited

U.S. PATENT DOCUMENTS

| | | |
|---|---|---|
| 4,136,093 | 1/1979 | Bonhard et al. ............ 530/385 |
| 4,336,248 | 6/1982 | Bonhard et al. ............ 530/385 |
| 4,377,512 | 3/1983 | Ajisaka et al. ............. 530/385 |
| 4,529,719 | 11/1984 | Tye ............................. 514/6 |
| 4,831,012 | 5/1989 | Estep ........................... 514/6 |

FOREIGN PATENT DOCUMENTS 8504407 10/1985 WIPO .

*Primary Examiner*—Michael G. Wityshyn
*Assistant Examiner*—C. Sayala
*Attorney, Agent, or Firm*—Pollock, Vande Sande & Priddy

[57] ABSTRACT

A pyridoxylated hemoglobin is prepared in a one-step, one-container process from red blood cells or essentially stroma-free hemoglobin by suspending the cells or hemoglobin in an aqueous medium, adding a chemical reducing agent and a pyridoxylating agent, and heating the reaction mixture obtained at a certain temperature for a certain time, while maintaining reducing conditions in the reaction medium.

20 Claims, No Drawings

ONE-STEP, ONE-CONTAINER METHOD FOR THE PREPARATION OF PYRIDOXYLATED HEMOGLOBIN

The present invention relates to a method for the preparation of a pyridoxylated modified hemoglobin. More particularly, the invention relates to such a method which is easier and less cumbersome to carry out than the methods known from the prior art.

Hemoglobin is the oxygen transporting protein of the red blood cells and makes up about 30 percent of the cell. The protein comprises four units, two alpha and two beta units, which are bonded together to a tetramer inside the cell. Inside the red cell, the hemoglobin is kept as a tetramer of two $\alpha$-chains and two $\beta$-chains. When free in plasma, hemoglobin dissociates and two dimers ($\alpha$, $\beta$) are bound to haptoglobin. Free hemoglobin in plasma will soon leave the circulation with a half-life of about 3 hours.

The oxygen affinity is modulated by pH, $CO_2$ concentration and the compound: 2,3-DPG (2,3-diphosphoglycerate) which is only available inside the red cell. Outside the cell the oxygen affinity of hemoglobin is high and therefore the ability to transfer oxygen to the tissue is low. Antigens which are bound to the cell wall surrounding the hemoglobin determine such factors as blood type, Rh factor and others. The cell wall residues obtained after lysis is called stroma.

Red blood cell substitutes are currently under development for use as oxygen transporting fluids. In "Blood substitues", Eds: Thomas M S Chang & Robert P Geyer; Marcel Dekker Inc. N.Y. 1989 (ISBN 0-847-8027-2) the present situation has been summarized.

It has been known for a long time that hemoglobin outside the cell has oxygen-transporting properties and can be given to patients regardless of their blood types. However, hemoglobin dissociates in the body into two alpha-beta units, which give rise to kidney dysfunction. Although this dysfunction is reversible, it can be very serious for patients who are already in a weakened state. Other side effects have also been known to occur.

W R Amberson (Biol Rev 12 p 48 (1937)) used red cell hemolysates as a blood substitute. It was nephrotoxic. The adverse effect was suggested by Rabiner et al (J Exp Med 126 p 1127 (1967)) to depend on the presence of stroma residues. However, even stroma-free hemoglobin solution had effects on the kidneys and was shown to give a transient decrease in creatinine clearance and urinary volume (G S Moss et al; Surg Gynecol Obstet 142 p 357 (1976); De Venuto et al; J Lab Clin Med 89 p 509 (1977) and Savitsky et al; Clin Pharm Ther 23 p 73 (1978)).

Different types of modifications of the hemoglobin molecule have been described in Methods in Enzymology Vol 76 (Hemoglobins); Editors S P Colowick, N O Kaplan, Academic Press N.Y. (1981). Benesch et al; Biochemistry Vol 11, No 19 p 3576–3582 (1972) described the modification most commonly used to decrease the oxygen affinity, by the incorporation of pyridoxal-5'-phosphate. This stabilizes the hemoglobin molecule in a configuration similar to the hemoglobin-DPG (diphosphoglycerate) complex inside the red cell. Lately the bispyridoxal tetraphosphate has been used for this type of modification (P E Keipert, A J Adenican, S Kwong & R E Benesch, Transfusion 29, p 768–773 (1989)).

Other compounds, e.g. inositol-hexaphosphate, can also be used for the modification of hemoglobin to obtain a product with lower oxygen affinity.

In U.S. Pat. Nos. 4,001,200; 4,001,401, 4,053,590 and 4,061,736, Bonsen et al have shown different routes to increase the molecular weight of hemoglobin and thus further stabilize the structure in order to increase the apparent half-life of the blood substitute based on hemoglobin.

A further problem in the administration of hemoglobin preparations lies in the absolute requirement that these preparations be free from microorganisms and viruses. Especially, it has been shown that viruses may be transmitted from blood donors to recipients.

If viruses in the hemoglobin are to be inactivated, the substantially cell-free hemoglobin solution is heated at a temperature from 45° to 85° C. while it is maintained in its deoxy form. This can be achieved by the use of reducing agents or by sparging the hemoglobin solution with an inert oxygen-free gas. The inactivation of viruses is usually carried out on the hemoglobin solution after the removal of the stroma and before the pyridoxylation step.

The polymerization of stroma-free hemoglobin and the inactivation of viruses by heat are described in more detail in the U.S. Pat. Nos. 4,826,811 and 4,831,012, the disclosures of which are hereby incorporated by reference. These two patents give a thorough overview of the state of the art and contain a great number of references to the prior art.

In the known processes for the preparation of pyridoxylated hemoglobin, red blood cells are used as the starting material. These cells are first washed and are then lysed with water or an aqueous buffer, and the hemoglobin is freed from the stroma. After this, the stroma is separated from the hemoglobin solution, for instance by microporous filtration.

All earlier workers have started their procedures by washing the red cells with saline, hypertonic salt solutions or other buffers to obtain as pure red cells as possible before lysing the cells. After lysis, great efforts have been made to separate stroma and residual proteins from hemoglobin by centrifugation, ultracentrifugation and/or filtration. In some descriptions the hemoglobin is even crystallized before it is used as raw material for a blood substitute. The loss of hemoglobin is substantial in each of the steps used.

The stroma-free hemoglobin is subsequently pyridoxylated with a pyridoxylating agent, such as pyridoxal-5'-phosphate, preferably in the presence of a buffer and at a temperature below 10° C. During the process, care must be taken to keep the reaction system free from oxygen, for instance by deoxygenating the reaction solution with an inert gas. Also, at the end of the reaction, a reducing agent, such as sodium borohydride, is preferably added to the deoxygenated solution. The stroma-free, pyridoxylated hemoglobin obtained in this manner may then be polymerized, for instance with glutaraldehyde.

These known processes for the preparation of pyridoxylated hemoglobin suffer from a number of disadvantages. A number of separate reaction steps are necessary, which lower the yield and increase the risk of bacterial contamination. A greater number of process steps also increases the overall costs of the process. Thus, in the first step of the know process i.e. the washing of the red blood cells, product losses of about 30 percent are usual. Also, the washing step is quite delicate, as the blood cells are very sensitive, and furthermore, the risk of bacterial contamination is very great, as the blood and the red blood cells are an excellent nutrient medium for microorganisms. This has made it nearly impossible to carry out the washing step on an industrial scale.

Thus, there exists a need for a process for the preparation of a pyridoxylated hemoglobin which is essentially free from microorganisms and viruses, where said process is simple to carry out and comprises a smaller number of process steps in comparison with the prior art processes. This is achieved by the process of the present invention.

Surprisingly, it has been found that by the process described below, the lysis, heat treatment and pyridoxylation can be combined into one step with good overall yield. The pyridoxylated hemoglobin can be used in the production of a blood substitute, e.g. according to Sehgal et al, U.S. Pat. No. 4,826,811, which is polymerized with glutaraldehyde and purified to contain only a small amount of tetramer (<2 percent), or in the production of dimerized or polymerized hemoglobin by other known methods.

According to the present invention, a pyridoxylated hemoglobin is prepared by providing an aqueous suspension of red blood cells or of substantially stroma-free hemoglobin, adding a chemical reducing agent and pyridoxal-5'-phosphate, and heating the reaction mixture thus obtained at a temperature between 20° and 85 degrees C. for a time between 0.5 and 15 hours.

In a preferred embodiment of the process of the invention, it is possible to use a suspension of red blood cells directly as a starting material, so that the washing step of the prior art is avoided. The subsequent addition of a reducing agent, pyridoxylation and heat treatment may all be carried out in the same reaction vessel without any intermediate separation or other working-up steps. Thus, the process of the invention is essentially a one-step, one-container process, which is a great simplification of the process and gives a diminished risk of product losses and contamination by micro-organisms and viruses.

It is also possible to use as a starting material blood cells which have been subjected to a lysis and from which the stroma has been removed completely or partially. In this case, the cells may, but need not have been washed beforehand. Thus, the advantages mentioned above are also obtained in this embodiment of the invention.

Although it is not desired to limit the invention by any theory, it is assumed that the reaction product formed in the pyridoxylation step is a Schiff base, which is normally unstable. In the prior art process, this base has been stabilized by the subsequent addition of sodium borohydride. In the process of the present invention, however, the reducing agent first added makes the reaction environment sufficiently reducing to stabilize the Schiff base formed in the pyridoxylation step. Also, the hemoglobin is maintained in its deoxy form, which is necessary for the pyridoxylation reaction, and which also is sufficiently stable not to be denatured in the heating step. After the pyridoxylation and heating, the product obtained is sufficiently stable to be used in the polymerization step.

When the hemoglobin in solution and the red cells still present are subjected to the heating step, the residual cells are lysed and the pyridoxylation reaction with the free reduced hemoglobin is completed at the same time as the viruses present are inactivated, and other non-hemoglobin proteins are denatured and precipitated. This makes the removal of such proteins easy, and is a further advantage of the process of the invention. It may also be noted that the reducing agent present during the heating step usually has bactericidal properties and contributes to the inactivation of microorganisms.

The pyridoxylation and heating should be carried out under reducing conditions, to ensure that the hemoglobin is maintained in its deoxy form. The presence of the reducing agent in the reaction medium ensures that the reducing environment is maintained, and this means that the atmosphere above the reaction medium does not have to be strictly free from oxygen. This is another important advantage in the process of the invention. Also, once the pyridoxylation and heating have been carried out, the requirement for reducing conditions is no longer so strict in the subsequent steps.

The polymerization of the pyridoxylated hemoglobin may be carried out in ways known from the literature, such as the previously mentioned U.S. Pat. No. 4,826,811. Before the polymerization, a salt which forms a precipitate with the reducing agent, such as a soluble calcium salt, for example calcium chloride, and optionally a buffer substance may be added to the reaction mixture from the heating step to precipitate such salts as sulfite, after which precipitated materials are removed, for instance by centrifugation. From the remaining solution, dissolved salts are removed, for instance by gel filtration or dialysis. A desalting process may also be carried out as an alternative to the precipitation. The polymerization is then carried out in a known way with the use of a known reagent, such as glutaraldehyde, or other agents described in the literature for dimerization or polymerization of hemoglobin.

In the process of the invention, a suitable starting material is a fresh or outdated red cells concentrate, i.e. red cells which have been stored too long to be permitted for transfusion. Fresh or outdated human blood may also be used. The red cells are suspended in a cold aqueous medium, such as pyrogen-free water, and the temperature may rise to room temperature during the treatment. The amount of aqueous medium is not critical, and may be from 1 to 20 volumes, preferably about 5 volumes, per volume of cell slurry. The aqueous slurry is then buffered to a pH of about 8, for example by the addition of disodium hydrogen phosphate to a concentration of about 0.03M. Of course, it is also possible to use a buffer solution directly as the suspension medium for the blood cells. In this suspension, the blood cells are partially lysed.

The chemical reducing agent is then added to the buffered cell suspension. As the reducing agent, a dithionite, bisulfite, metabisulfite or sulfite of an alkali metal or ammonium can be used. Among these agents, sodium dithionite is preferred. The reducing agent is added in a sufficient amount to ensure that all of the hemoglobin will be in the deoxy form and reducing conditions will be maintained during the whole process. The preferred reducing agent sodium dithionite is so strongly reducing that it does not require an oxygen-free atmosphere in the reaction vessel. Others of the reducing agents mentioned may have to be supported in their reducing power by an essentially oxygen-free atmosphere in the reaction vessel. The necessary reaction conditions in this respect can easily be determined by a person skilled in the art.

Generally, the reducing agent is added in an amount which corresponds to a molar ration between the hemoglobin and the reducing agent from 1:5 to 1:100, and preferably then from 1:10 to 1:60. For sodium dithionite, a concentration of about 0.03M has turned out to be suitable.

For the pyridoxylation, a pyridoxylating agent, such as pyridoxal-5'-phosphate is added to the cell suspension containing the reducing agent. The pyridoxal-5'-phosphate maybe added as a solution, usually in a buffer, preferably a TRIS buffer. Generally, the pyridoxal-5'-phosphate is added in an amount which corresponds to a molar ratio between the hemoglobin and the pyridoxal-5'-phosphate from 1:1 to 1:12, and preferably then from 1:4 to 1:8. A molar ratio between hemoglobin and pyridoxal-5-phosphate of about 1:6 has turned out to be suitable.

The pyridoxylation process is completed during the heat treatment. The time for the pyridoxylation reaction may be from about half an hour to about 10 hours, depending on the specific details and apparatus for the process.

During the pyridoxylation, the hemoglobin is subjected to a heat treatment. In this treatment, viruses and microorganisms are largely inactivated and non-hemoglobin proteins are also precipitated to a large extent, which facilitates their subsequent removal. The lysis of the blood cells is also made complete. During the heat treatment, the hemoglobin should be in the deoxy form and this is usually ensured by the presence of the reducing agent. The heating should be carried out at a temperature within the range of 20° to 85° C., preferably at 60° to 80° C., and especially at about 70° C., for a time of about 10 hours. Shorter or longer times may also be used, and it is within the competence of a person skilled in the art to determine a suitable time for the treatment on the basis of simple routine tests for the presence of microorganisms or viruses.

As the reducing agent is still present in the reaction medium during the heating step, this contributes to maintain reducing conditions during this step. Furthermore, an atmosphere of an inert, oxygen-free gas may be present, such as nitrogen or argon, although this is not always strictly necessary.

It may also be noted that the preferred reducing agent, sodium dithionite, has strongly bactericidal properties. This contributes to the inactivation of bacteria.

After the heating step, the reaction mixture should be treated to remove such materials as inorganic salts, inactivated microorganisms and denatured non-hemoglobin proteins. For this, a salt may be added which forms a precipitate with the reducing agent used, such as a soluble calcium salt, for example calcium chloride. Also, a buffering substance may optionally be added. Additionally or as an alternative, the reaction mixture may be desalted, for instance by gel filtration or dialysis.

When the preferred reducing agent sodium dithionite has been used, calcium chloride may be added to a concentration of, for example, about 0.03M, to precipitate sulfites formed from the dithionite, followed by a subsequent desalting treatment. The reaction medium is then centrifuged to remove precipitated organic and inorganic materials. After this, dissolved salts may be removed by such processes as gel filtration or dialysis.

After the pyridoxylation, the hemoglobin thus treated is subjected to a polymerization. This polymerization is carried out in way known per se, and is described in, for example, U.S. Pat. No. 4,826,811. As a polymerization agent is used a dialdehyde, preferably glutaraldehyde, in an aqueous solution. One way of carrying out the polymerization is to arrange a solution of glutaraldehyde and a solution of the pyridoxylated hemoglobin on each side of a semi-permeable membrane. The glutaraldehyde can migrate through the membrane, while the big hemoglobin molecules cannot, and in this way a controlled polymerization reaction is obtained. The reaction is continued until a suitable molecular weight of the polymer has been attained. This can take up to ten hours.

The hemoglobin polymer obtained after purification is essentially free from the undesired hemoglobin tetramer, and contains no more than about 2 weight percent of this tetramer, based on the total amount of hemoglobin. The product is therefore substantially free from the harmful side effects associated with the tetramer.

After the polymerization, the hemoglobin product obtained may be formulated into a suitable dosage form for administration to patients. Such dosage forms may also contain additives which are well-known as such in the art.

The invention is further illustrated by the following examples, which, however, do not serve to limit the invention in its scope.

EXAMPLE 1

To 100 grams of red blood cells containing about 30 grams of hemoglobin is added 500 ml of 0.03M solution of disodium hydrogen phosphate at pH 8.5. After this, sodium dithionite is added in an amount to give a concentration of 0.03M, which corresponds to a molar ratio between the hemoglobin and the sodium dithionite of about 1:32, and pyridoxal-5'-phosphate dissolved in a TRIS buffer, adjusted to pH 8.5. The molar ratio between the hemoglobin and the pyridoxal-5'-phosphate is adjusted to 1:6. At this stage, the concentration of hemoglobin is about 3.5 weight percent, which contains about 1 weight percent of methemoglobin and 97–99 weight percent of deoxy-hemoglobin.

The reaction mixture obtained is then heated at about 70° C. for about 10 hours in a closed glass vessel. After the heat treatment, the concentration of methemoglobin is 1–2 weight percent, and the yield of pyridoxylated hemoglobin is about 96%.

The above reactions are carried out in a closed vessel, and the reducing environment is assured by the presence of the sodium dithionite. After the heat treatment, however, the following steps may be carried out openly in the presence of air, and preferably at a temperature of about 5° C.

To the reaction mixture after the heating step is added calcium chloride to a concentration of 0.03M. This precipitates the sulfite formed from the sodium dithionite, together with non-hemoglobin proteins which have been denatured during the heat treatment. The precipitated materials are removed by centrifugation. After this step, the concentration of methemoglobin is about 2 weight percent, and 50 to 80 percent of the hemoglobin has been transformed into oxyhemoglobin.

The hemoglobin solution is then desalted on a column of Sephadex ® G-25, (from Pharmacia, Uppsala, Sweden) which has been equilibrated with 0.14M NaCl.

The yield of the pyridoxylation reaction, according to electrophoresis, is found to be 100%, and the $P_{50}$ for $O_2$ is 22–25 tort. The Hill coefficient is 2.0–2.2. In a chromatographic analysis, the product agrees with data for pyridoxylated hemoglobin from the literature.

The pyridoxylated hemoglobin product obtained may then be polymerized with glutaraldehyde in a manner known per se, for example as described in U.S. Pat. No. 4,826,811.

EXAMPLE 2

100 grams of red blood cells were washed with 3×500 ml saline solution. After centrifugation, the washed cells were lysed by the addition of 500 ml of distilled water, and stroma was removed by centrifugation and filtration.

To the solution were added disodium hydrogen phosphate and sodium dithionite, each in an amount to give a concentration of 0.03 moles per litre. After this, pyridoxal-5'-phosphate was added in an amount to give a molar ratio between hemoglobin and pyridoxal-5'-phosphate of about 1:6, and the resulting solution was heated in a closed vessel at 70° C. for ten hours.

Calcium chloride was added to precipitate sulfates and sulfites formed in the reaction, and after centrifugation, the hemoglobin solution was desalted by ultrafiltration or chromatography.

$P_{50}$ for $O_2$ was determined and found to be 25 tort. The Hill coefficient was 2.0–2.2. By electrophoresis, it was shown that the incorporation of pyridoxal-5'-phosphate was complete.

Typical values for the solution were as follows:

| $O_2$—Hb | CO—Hb | Met—Hb | Deoxy—Hb (Hb = hemoglobin) |
|---|---|---|---|
| 97% | 0.5% | 1.0% | 1.5% |

EXAMPLE 3

Example 2 was repeated, with the differences that the blood cells were lysed in 10 volumes of water, and that the stroma was filtered off. The filtrate was then buffered with disodium hydrogen phosphate to a concentration of 0.03M and a pH of 8.5.

The pyridoxal-5'-phosphate was added as an aqueous solution with its pH adjusted to 8.5, but no TRIS buffer was used.

The hemoglobin product obtained had the same properties as that in example 2.

We claim:

1. An industrial method for the preparation of pyridoxylated hemoglobin by treating red blood cells with a chemical reducing agent and with pyridoxal-5'-phosphate, characterized in that the chemical reducing agent and the pyridoxal-5'-phosphate are mixed with the red blood cells at the same time, that the mixture is heated to a temperature between 20° and 85° C. for a time of 0.5 to 15 hours, and that the preparation process is carried out as a one-step and one-container process.

2. The method of claim 1, characterized in that the reducing agent is a dithionite, bisulfite, metabisulfite or sulfite of an alkali metal or of ammonium.

3. The method of claim 2 characterized in that the reaction mixture is heated at a temperature between 60° and 80° C. for a time of about 10 hours.

4. The method of claim 2 characterized in that the pyridoxal-5'-phosphate is added in an amount which corresponds to a molar ratio between the hemoglobin and the pyridoxal-5-'phosphate from 1:1 to 1:12.

5. The method of claim 4 wherein said ratio is 1:4 to 1:8.

6. The method of claim 2 characterized in that the chemical reducing agent is added in an amount which corresponds to a molar ratio between the hemoglobin and the reducing agent from 1:5 to 1:100.

7. The method of claim 6 wherein said ratio is 1:10 to 1:60.

8. The method of claim 1, characterized in that the reducing agent is sodium dithionite.

9. The method of claim 1, characterized in that the reaction mixture is heated at a temperature between 60° and 80 degrees C. for a time of about 10 hours.

10. The method of claim 9 wherein said temperature is about 70° C.

11. The method of claim 1, characterized in that the chemical reducing agent is added in an amount which corresponds to a molar ratio between the hemoglobin and the reducing agent from 1:5 to 1:100.

12. The method of claim 11 wherein said ratio is 1:10 to 1:60.

13. The method of claim 1, characterized in that the pyridoxal-5'-phosphate is added in an amount which corresponds to a molar ratio beteween the hemoglobin and the pyridoxal-5'-phosphate from 1:1 to 1:12.

14. The method of claim 13 wherein said ratio is 1:4 to 1:8.

15. The method of claim 1, characterized in that reducing conditions are maintained in the reaction medium during the reactions.

16. The method of claim 1, further characterized by adding to the reaction mixture a salt which forms a precipitate with the reducing agent, and optionally a buffering substance, and/or subjecting the reaction mixture to a desalting treatment, after which precipitated materials are separated.

17. The method of claim 16 wherein said salt is calcium chloride.

18. The method of claim 16, characterized in that after the removal of precipitated materials and dissolved salts, the hemoglobin is dimerized or polymerized.

19. The method of claim 18, characterized in that the hemoglobin is dimerized or polymerized with glutaric aldehyde.

20. The method of claim 18, characterized in that the polymerized hemoglobin has a content of hemoglobin tetramer which is less than 2 weight percent of the total amount of hemoglobin.

* * * * *